(12) United States Patent
Lin

(10) Patent No.: US 7,798,424 B2
(45) Date of Patent: Sep. 21, 2010

(54) AUTOMATIC AIR FRESHENER SPRAYING DEVICE

(76) Inventor: Po-Hui Lin, No. 9, Lane 96, Sec. 8, Ho-Ping East Road, Taipei (TW)

( * ) Notice: Subject to any disclaimer, the term of this patent is extended or adjusted under 35 U.S.C. 154(b) by 173 days.

(21) Appl. No.: 12/222,757

(22) Filed: Aug. 15, 2008

(65) Prior Publication Data
US 2010/0038452 A1    Feb. 18, 2010

(51) Int. Cl.
*A62C 31/00* (2006.01)
(52) U.S. Cl. .......................... 239/305; 239/69; 239/70; 239/304; 239/332; 239/333; 239/337; 222/129; 222/333; 222/402.13; 222/646; 222/649
(58) Field of Classification Search .................. 239/69, 239/70, 303–305, 332, 333, 337; 222/129, 222/135, 333, 402.13, 402.15, 646, 649
See application file for complete search history.

(56) References Cited
U.S. PATENT DOCUMENTS

| | | | | |
|---|---|---|---|---|
| 3,589,563 A | * | 6/1971 | Carragan et al. | 239/70 |
| 3,677,441 A | * | 7/1972 | Nixon et al. | 222/135 |
| 3,739,944 A | * | 6/1973 | Rogerson | 222/649 |
| 5,249,718 A | * | 10/1993 | Muderlak | 239/70 |
| RE34,847 E | * | 2/1995 | Muderlak et al. | 239/70 |
| 6,036,108 A | * | 3/2000 | Chen | 239/69 |
| 6,267,297 B1 | * | 7/2001 | Contadini et al. | 239/337 |

* cited by examiner

*Primary Examiner*—Steven J Ganey
(74) *Attorney, Agent, or Firm*—Rosenberg, Klein & Lee

(57) ABSTRACT

An automatic air freshener spraying device includes a front cover, a base, two air freshener bottles and a press driving device, and a motor of the press driving device is pivotally coupled to the driving gear, such that when the driving gear rotates clockwise or anti-clockwise at the motor, the driving gear with the transmission of the gear set pushes a protruding member at the bottom of one of the left and right sides of a large fan-shaped gear to obtain a larger instant pressing force, and a set of press driving devices are used for controlling the motor to rotate clockwise or anti-clockwise, and either the left or right air freshener bottles is pressed to spray an air freshener from an air freshener nozzle of the left air freshener bottle or the right air freshener bottle, so as to provide a uniform misty spray.

1 Claim, 6 Drawing Sheets

AUTOMATIC AIR FRESHENER SPRAYING DEVICE

BACKGROUND OF THE INVENTION

1. Field of the Invention

The present invention relates to an automatic air freshener spraying device including a front cover, a base, two air freshener bottles and a press driving device, and a motor of the press driving device is pivotally coupled to the driving gear, such that when the driving gear rotates clockwise or anti-clockwise at the motor, the driving gear with the transmission of the gear set pushes a protruding member at the bottom of one of the left and right sides of a large fan-shaped gear to obtain a larger instant pressing force, and a set of press driving devices are used for controlling the motor to rotate clockwise or anti-clockwise, and either the left or right air freshener bottles is pressed to spray an air freshener from an air freshener nozzle of the left air freshener bottle or the right air freshener bottle, so as to provide a uniform misty spray.

2. Description of the Related Art

As economy progresses, our living quality is improved constantly, and people place increasingly more emphases on spiritual life as well as physical life and look for an excellent living environment. To keep our living environment such as an office, a room and a car free of peculiar odors and air pollution to improve working efficiency and maintain a better mental status, we generally install air-conditioners and air purifiers to purify air or air freshener, electric fragrant emitting plate, perform to eliminate peculiar odors indoors. Various different products for eliminating peculiar smells and odors from air are available in the market, and thus it is an important subject for manufacturers to develop an air freshener spraying device with a simple structure and automatic air freshener spraying function for attracting consumers' purchasing desire.

A common air freshener spraying device available in the market generally includes a bias cam pivotally coupled to a motor, and when the bias cam is rotated at the motor, a nozzle of an air freshener bottle is pressed to spray air freshener. The nozzle of the air freshener bottle usually requires an instant large pressing force to spray misty air freshener, but the conventional spraying device adopting the bias cam and requiring a pressing force cannot meet the user requirement or spray air freshener in a misty form, and causing a serious drawback of spraying air freshener in a water-drop form.

In addition, a general conventional air freshener bottle comes with a fixed specific capacity (approximately 3000 times/bottle). If the nozzle of the air freshener bottle is pressed once every 15 minutes, each air freshener may last about a month, and it is necessary to replace an air freshener bottle refill, which causes inconvenience to users and incurs a higher labor cost.

In view of the shortcomings of the prior art, the inventor of the present invention based on years of experience in the related industry to conduct extensive researches and experiments, and finally developed an automatic air freshener spraying device in accordance with the present invention to overcome the shortcomings of the prior art.

SUMMARY OF THE INVENTION

Therefore, it is a primary objective of the invention is to provide an automatic air freshener spraying device, comprising a front cover, a base, two air freshener bottles and a press driving device, and a motor of the press driving device is pivotally coupled to the driving gear, such that when the driving gear rotates clockwise or anti-clockwise at the motor, the driving gear with the transmission of the gear set pushes a protruding member at the bottom of one of the left and right sides of a large fan-shaped gear to obtain a larger instant pressing force, and a set of press driving devices are used for controlling the motor to rotate clockwise or anti-clockwise, and either the left or right air freshener bottles is pressed to spray an air freshener from an air freshener nozzle of the left air freshener bottle or the right air freshener bottle, so as to provide a uniform misty spray.

The advantages and characteristics of the present invention will become apparent with the detailed description of the following preferred embodiments with accompanying drawings as follows.

With reference to FIGS. 1 to 3 for an automatic air freshener spraying device of the present invention, the automatic air freshener spraying device 10 comprises a front cover 11, a base 12, two air freshener bottles 13 and a press driving device.

The front cover 11 is a hollow frame.

The base 12 is a hollow frame, including two air freshener bottles 13 disposed at the bottom in the base 12, and a nozzle 14 disposed at the top of the air freshener bottle 13.

The press driving device as shown in FIGS. 4 and 5 comprises a fixing plate 2, a motor 3, a driving gear 31, a plurality of large gears 32, 34, 36, a plurality of small gears 33, 35, 37 and a large fan-shaped gear 4, and the fixing plate 2 is a polygonal plate having a circular hole 21 disposed separately at corners, and the fixing plate 2 includes a plurality of camshafts 22, 23, 24, 25 disposed thereon for positioning a gear set, and the motor 3 is coupled to a side of the fixing plate 2, and a transmission shaft 30 of the motor 3 is passed through a driving gear 31, and the camshaft 23 is passed through a small gear 33, a large gear 32, and the large gear 32 is engaged with the driving gear 31, and the camshaft 24 is passed through a small gear 35, a large gear 34, and the large gear 34 is engaged with the small gear 33, and the camshaft 25 is passed through a small gear 37 and a large gear 36, and the large gear 36 is engaged with the small gear 35, and the large fan-shaped gear 4 includes a protruding member 43, 44 disposed separately on both left and right sides at the bottom edge, and the large fan-shaped gear 4 is passed through and pivotally coupled to the camshaft 22 by the shaft sleeve 41, and an arc gear rack 42 of the large fan-shaped gear 4 is engaged with the small gear 37 to form a press driving device, and the fixing plate 2 is screwed to the top of the base 12 by securing a fixing screw 15 into the circular hole 21, and the front cover 11 is covered onto the exterior of the base 12 and integrally coupled with the base 12 to form an automatic air freshener spraying device.

In the present invention, the base 12 includes a control circuit component and a battery module (not shown in the figure), and the control circuit component and the battery module are prior arts, and thus will not be described here.

DETAILED DESCRIPTION OF THE PREFERRED EMBODIMENTS

Figure 1:
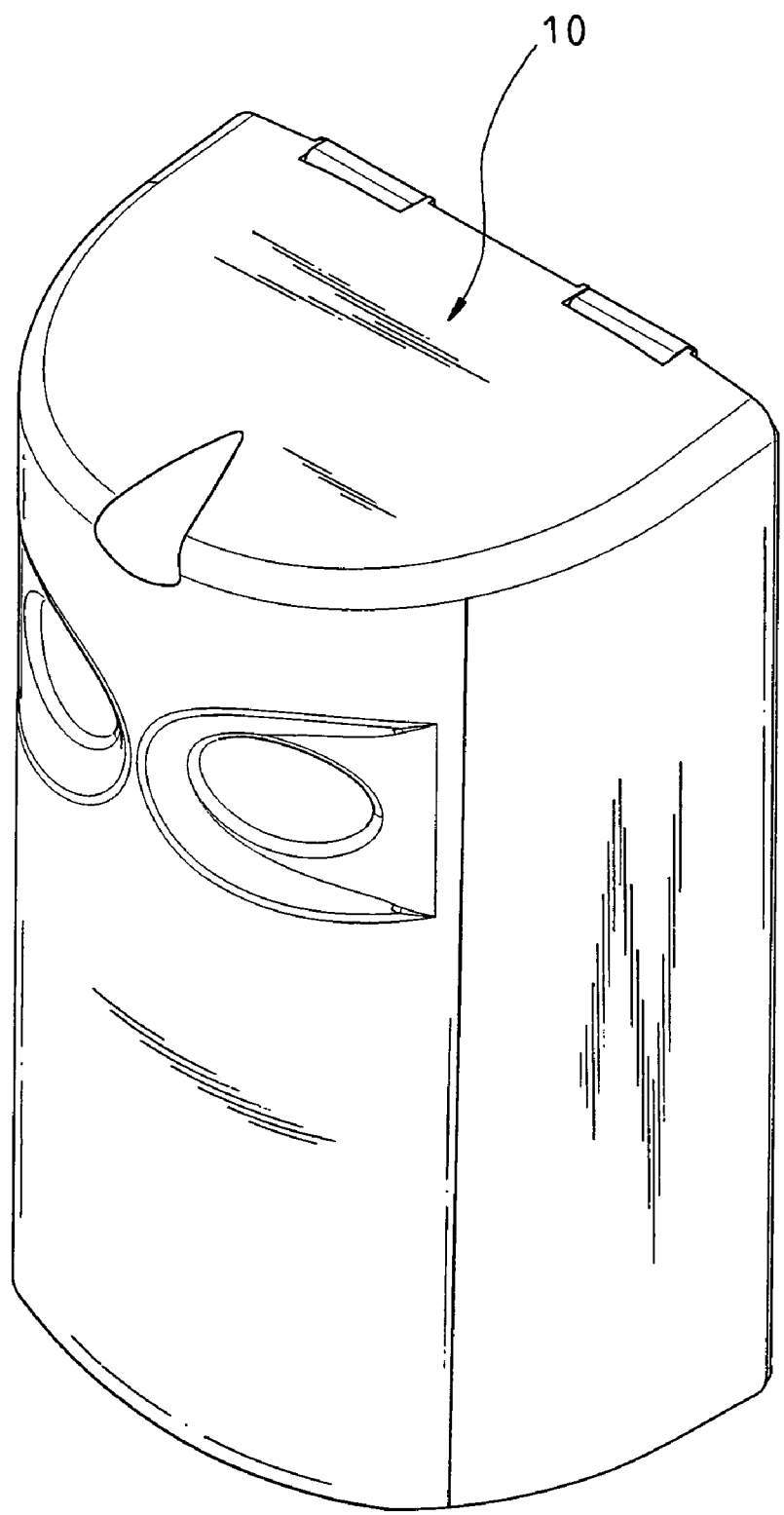
FIGS. 1 to 3 are schematic views of a structure of the present invention.
Figure 2:
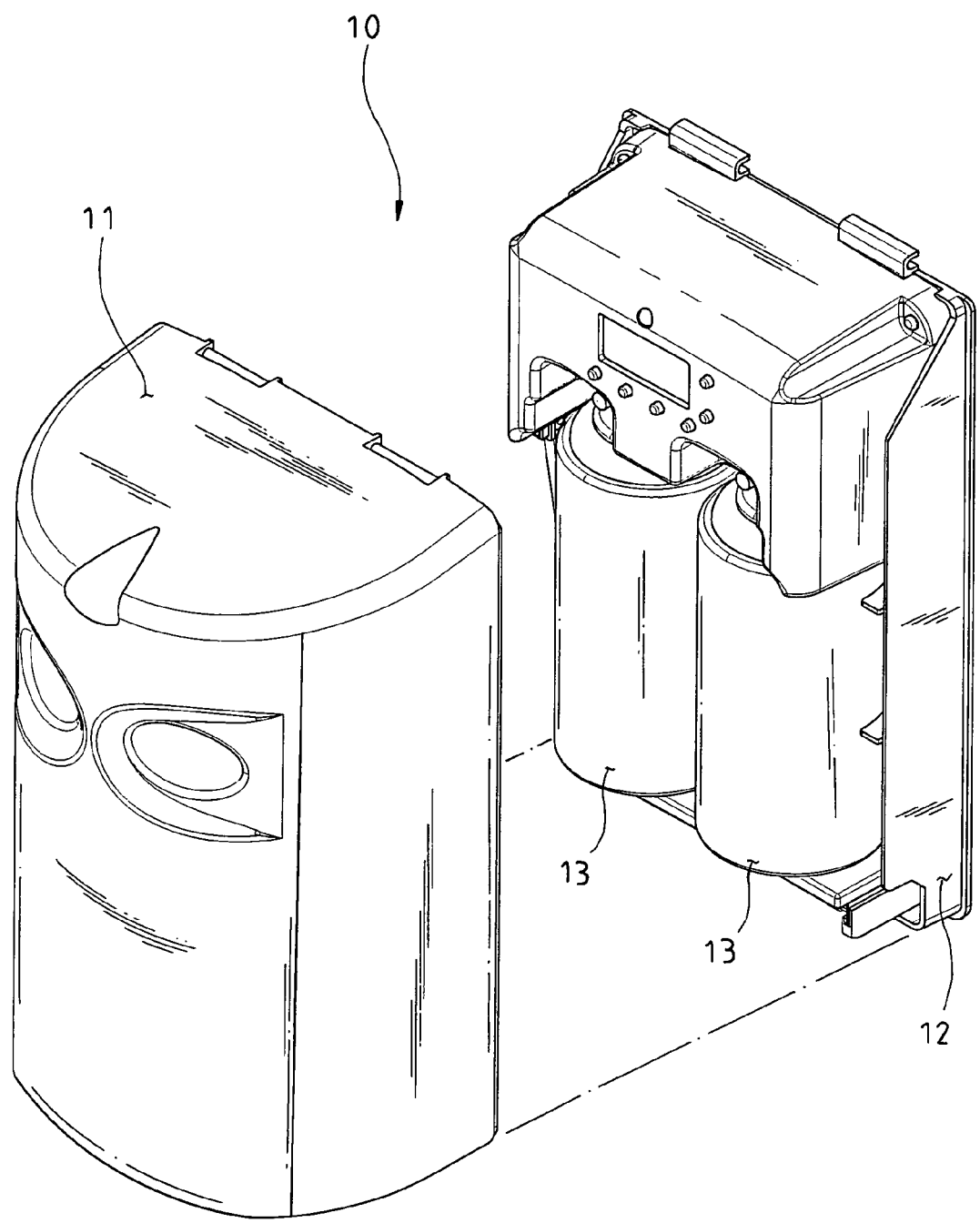
Figure 3:
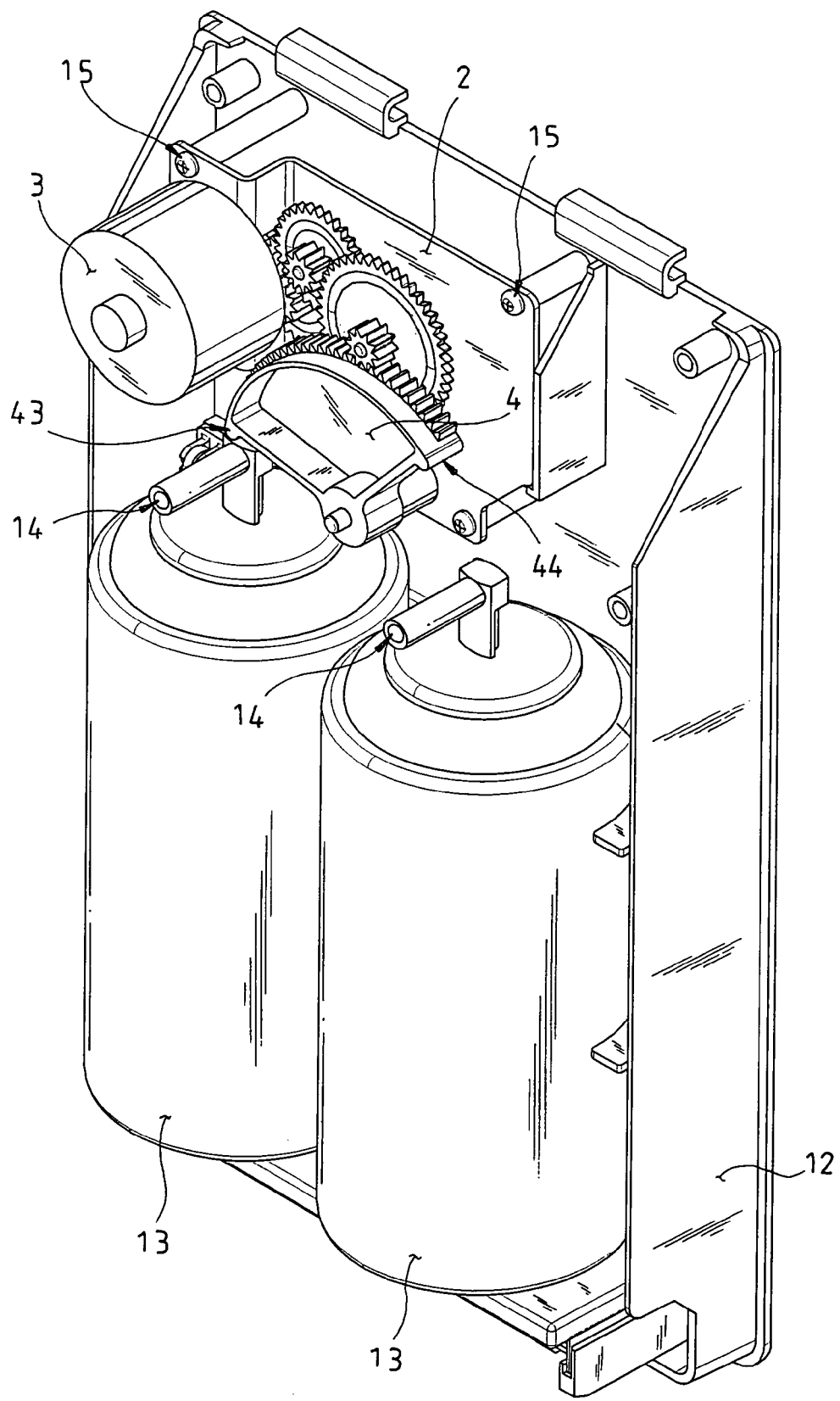
Figure 4:
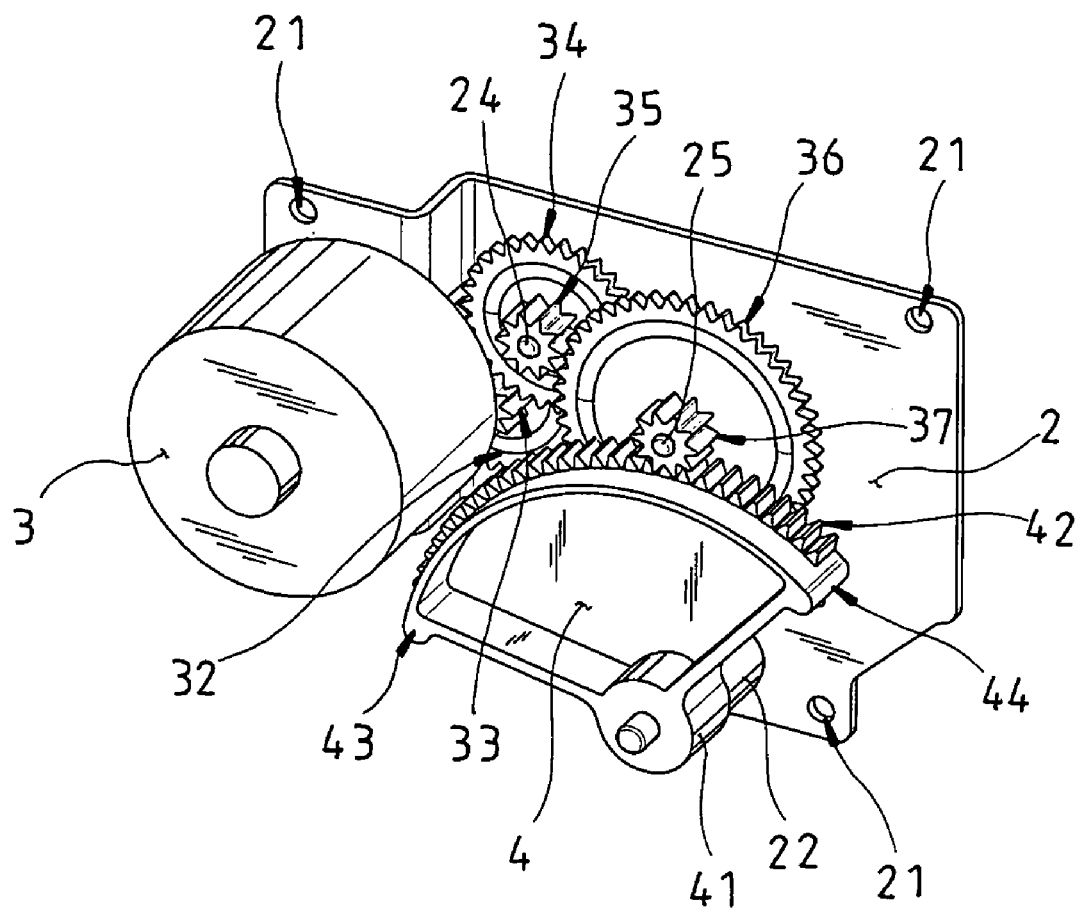
FIGS. 4 and 5 are schematic views of a structure of a driving gear set of the present invention.
Figure 5:
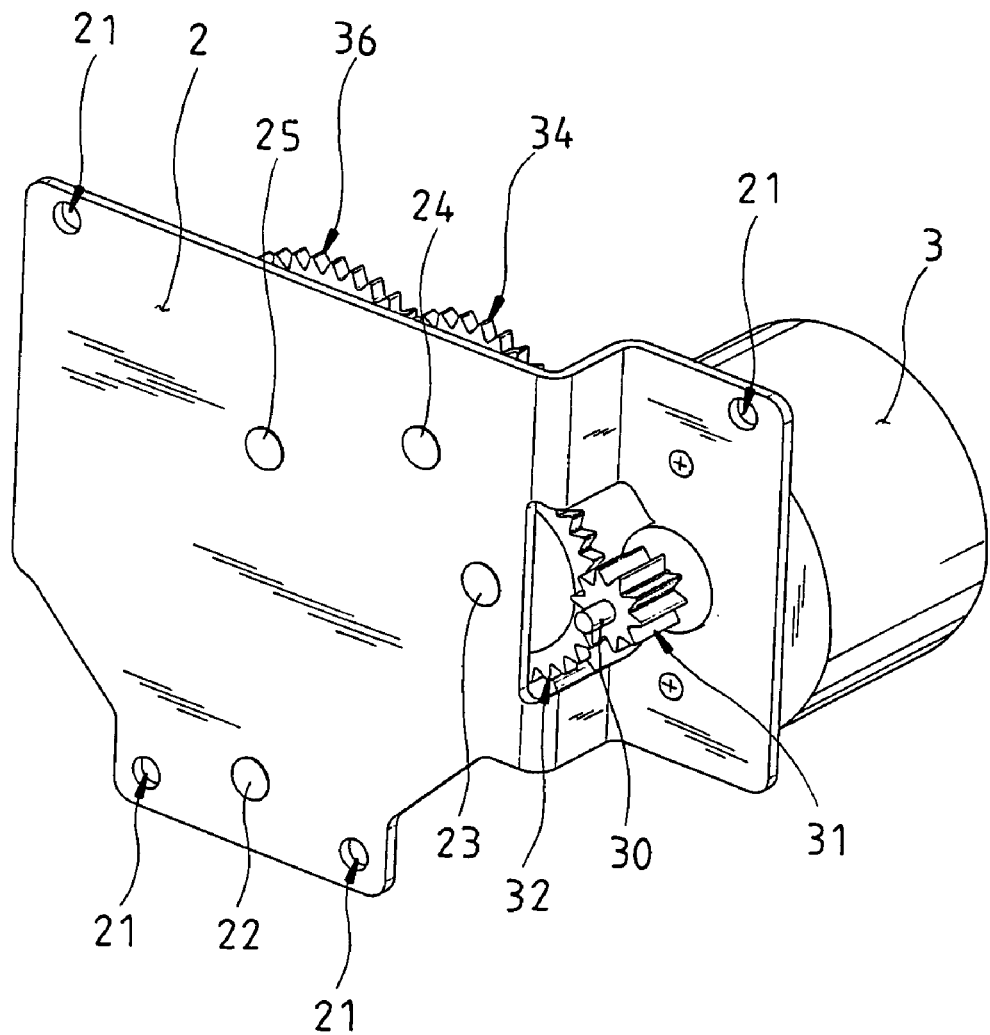
Figure 6:
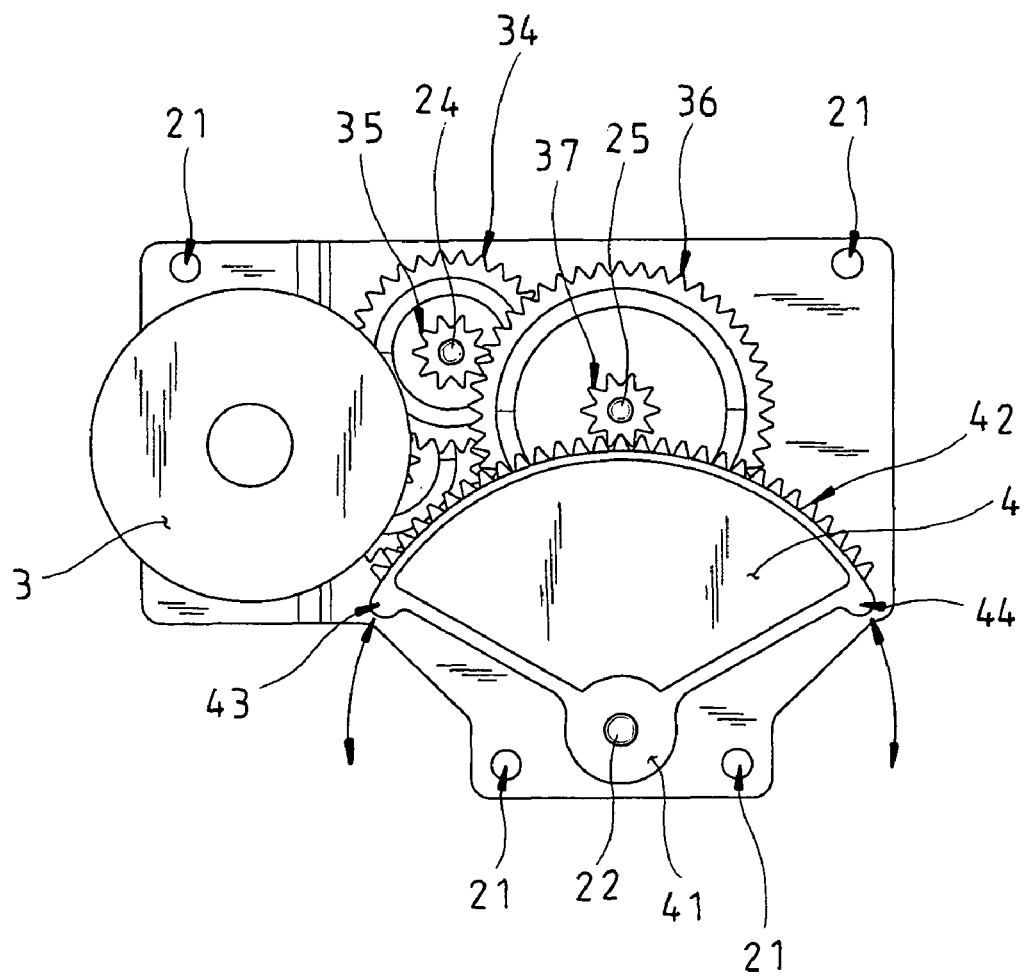
FIG. 6 is a schematic view of pressing a large fan-shaped gear of the present invention.

With reference to FIGS. 3 to 6 for the present invention, a motor 3 is installed on a press driving device, and a control circuit component is provided for controlling the motor to rotate or stop. If the motor 3 is rotated clockwise, a driving gear 31 is also rotated clockwise, such that the driving gear 31 drives a large gear 32 and a small gear 33 to rotate anti-clockwise, and the small gear 33 drives a large gear 34 and a small gear 35 to rotate clockwise, and the small gear 35 drives a large gear 36 and a small gear 37 to rotate anti-clockwise, and the small gear 37 drives a large fan-shaped gear 4 to rotate clockwise, and a protruding member 44 disposed at the bottom on the right side of the large fan-shaped gear 4 is pushed downward. If a nozzle 14 disposed on the right side of an air freshener bottle is pressed, air freshener is sprayed from the nozzle 14.

If the motor 3 is rotated anti-clockwise, the driving gear 31 will be rotated anti-clockwise as well, so that the driving gear 31 drives a large gear 32 and a small gear 33 to rotate clockwise, and the small gear 33 drives a large gear 34 and a small gear 35 to rotate anti-clockwise, and the small gear 35 drives a large gear 36 and a small gear 37 to rotate clockwise, and the small gear 37 drives the large fan-shaped gear 4 to rotate anti-clockwise, and a protruding member 43 at the bottom on the left side of the large fan-shaped gear 4 is pushed downward, such that when the nozzle 14 of the left air freshener bottle is pressed, air freshener is sprayed from the nozzle 14.

With the transmission of the gear set of the invention, the protruding members 43, 44 at the bottom of both left and right sides the large fan-shaped gear 4 are pushed downward respectively by an instant larger pressing force. In the meantime, a set of press driving device is used for controlling the motor to rotate clockwise or anti-clockwise, and the air freshener bottle of either the left air freshener bottle or the right air freshener bottle is pressed to achieve a quick stable press of the nozzle for spraying air freshener in form of a uniform misty spray.

With the control circuit component of the invention, a press driving device is provided for controlling the motor to rotate clockwise or anti-clockwise, and when the left air freshener bottle is pressed and after the air freshener of the left air freshener bottle, the right air freshener bottle is pressed to extend and double the using time before a new air freshener bottle is replaced to enhance the practical application of the product.

With the control circuit component, a set of press driving device is provided for controlling the motor to rotate clockwise or anti-clockwise, the left air freshener bottle and the right air freshener bottle are pressed alternately to extend and double the using time before a new air freshener bottle is replaced to enhance the practical application of the product.

In summation of the description above, the present invention improves over the prior art, and complies with the requirements of patent application, and thus is duly filed for patent application.

What is claimed is:

1. An automatic air freshener spraying device (10), comprising a front cover (11), a base (12), two air freshener bottles (13) and a press driving device, wherein:
   the front cover (11) is a hollow frame;
   the base (12) is a hollow frame, having the two air freshener bottles (13) contained at the bottom in the base (12) and a nozzle (14) disposed at the top of each air freshener bottle (13);
   the press driving device comprises a fixing plate (2), a motor (3), a driving gear (31), a plurality of large gears, a plurality of small gears and a large fan-shaped gear (4), and the fixing plate (2) is a polygonal plate having a circular hole (21) separately disposed at corners, and the fixing plate (2) includes a plurality of camshafts for positioning a gear set, and the motor (3) is coupled to a side of the fixing plate (2), and a transmission shaft (30) of the motor (3) is passed through the driving gear (31), and a camshaft (23) is passed through a small gear (33) and a large gear (32), and the large gear (32) is engaged with the driving gear (31), and a camshaft (24) is passed through a small gear (35) and a large gear (34), and the large gear (34) is engaged with the small gear (33), and a camshaft (25) is passed through a small gear (37) and a large gear (36), and the large gear (36) is engaged with the small gear (35), and the large fan-shaped gear (4) includes a protruding member (43) disposed at the bottom of a left side and a protruding member (44) disposed at the bottom of a right side, and the large fan-shaped gear (4) is pivotally coupled to a camshaft (22) by a shaft sleeve (41), and an arc gear rack (42) of the large fan-shaped gear (4) is engaged with the small gear (37) to rotatively displace the large fan-shaped gear (4) responsive to rotation of the small gear 37, and the fixing plate (2) is screwed to the top of the base (12) by securing the fixing screw (15) into the circular hole (21), and the front cover (11) is covered onto the exterior of the base (12) and integrally coupled with the base (12).

* * * * *